(12) United States Patent
Srivastava et al.

(10) Patent No.: US 6,287,873 B2
(45) Date of Patent: *Sep. 11, 2001

(54) MICROBIOLOGICAL DESULFURIZATION OF SULFUR CONTAINING GASES

(75) Inventors: Kailish C. Srivastava; Seema Garg, both of Centreville; Daman S. Walia, Clifton, all of VA (US)

(73) Assignee: Arctech Inc., Chantilly, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/261,751

(22) Filed: Mar. 3, 1999

Related U.S. Application Data

(63) Continuation-in-part of application No. 08/651,793, filed on May 20, 1996, now Pat. No. 5,981,266.

(51) Int. Cl.[7] ................................. A61L 9/01; C12N 1/00
(52) U.S. Cl. .................. 436/266; 435/252.4; 435/266; 435/244; 435/245; 435/251; 435/252.1; 435/821; 435/822
(58) Field of Search .................................. 435/262, 266, 435/252.4, 821, 822, 244, 245, 251, 252.1

(56) References Cited

U.S. PATENT DOCUMENTS

| | | | |
|---|---|---|---|
| 4,002,727 | * 1/1977 | Sonoda et al. | 423/576.5 |
| 4,206,288 | * 6/1980 | Detz et al. | 435/267 |
| 4,666,852 | 5/1987 | Cork . | |
| 4,760,027 | * 7/1988 | Sublette et al. | 435/266 |
| 4,851,350 | * 7/1989 | Stevens, Jr. et al. | 435/262 |
| 4,879,240 | * 11/1989 | Sublette et al. | 435/252.1 |
| 5,217,615 | 6/1993 | Tyagi et al. | 210/611 |
| 5,232,676 | 8/1993 | Wolff et al. | 423/210 |
| 5,236,677 | 8/1993 | Torres-Cardona et al. | 423/230 |
| 5,250,102 | 10/1993 | Barnes et al. | 75/710 |
| 5,269,929 | * 12/1993 | Sublette et al. | 210/610 |
| 5,297,625 | 3/1994 | Premuzic et al. | 166/246 |
| 5,354,545 | 10/1994 | Buisman | 423/242.1 |
| 5,385,842 | 1/1995 | Weimer et al. | 435/262 |
| 5,593,889 | * 1/1997 | Valentine | 435/282 |

OTHER PUBLICATIONS

Microbial Control of the Production of Hydrogen Sulfide by Sulfate–Reducing Bacteria, Montgomery et al., Biotechnology and Bioengineering, vol. 35, pp. 533–539, (1990).
Microbial Desulfurization of Gases, Sublette et al., Biotechnology and Bioengineering Symp. No. 17 (1986), pp. 543–564.
Microbial Reduction of Sulfur Dioxide with Pretreated Sewage Sludge and Elemental Hydrogen as Electron Donors, Deshmane, et al., Applied Biochemistry and Biotechnology, vol. 39/40, (1993), pp. 739–752.
Microbial Removal of Sulfur Dioxide from a Gas Stream with Net Oxidation to Sulfate, Dasu et al., Applied Biochemistry and Biotechnology, vol. 20/21, (1989), pp. 207–220.
Oxidation of Hydrogen Sulfide by Flocculated *Thiobaccillus dentrificans* in a Continuous Culture Biotechnology and Bioengineering, vol. 37, (1991) pp. 497–504.
Oxidation of Hydrogen Sulfide by Mixed Cultures of *Thiobaccillus dentrificans* and Heterotrophs, Sublette et al., Biotechnology and Bioengineering, vol. XXIX, (1987) pp. 759–761.
Oxidation of Hydrogen Sulfide by Thiobaccilli, Cadenhead et al., Biotechnology and Bioengineering, vol. 35, (1990) pp. 1150–1154.
Oxidation of Hydrogen Sulfide by *Thiobaccillus dentrificans*: Desulfurization of Natural Gas, Biotechnology and Bioengineering, vol. XXIX, (1987) pp. 249–257.
Production of Microbial Biomass Protein from Autotrophic Fermentation of Hydrogen Sulfide, Sublette, Biotechnology and Bioengineering, vol. 32, (1988) pp. 408–409.
Reduction of Sulfur Dioxide by *Desulfovibrio Desulfuricans* in Co–culture with Fermentative Heterotrophs, Dasu et al., Biotechnology and Bioengineering, vol. 34, (1989) pp. 405–409.
Removal Kinetics of Hydrogen Sulfide, Methanethiol and Dimethyl Sulfide by Peat Biofilters, Hirai et al., Journal of Fermentation and Bioengineering, vol. 70, No. 5, (1990) pp. 334–339.
Immobilization of an Autotrophic Bacterium by Coculture with Floc–Forming Heterotrophs, Ongcharit, et al., Biotechnology and Bioengineering, vol. 33, (1989), pp. 1077–1080.
Immobilization of *Thiobacillus denitrificans* for the Oxidation of Hydrogen Sulfide in Sour Water, Applied Biochemistry and Biotechnology, vol. 20/21 (1989) pp. 675–686.
Kinetics of Chemical and Biological Sulfide Oxidation in Aqueous Solutions, Buisman, et al. (1990). *(not included).
Biotechnological Process for Sulfide Removal with Sulfur Reclamation, Buisman, et al., ACTA Biotechnology, vol. 9, pp. 255–267, (1990). *(not included).
K.C. Srivastava, "Biological Removal of $H_2S$ From Sour Natural Gas", Proc. 1992 GRI Liquid Redox Sulfur Recovery Conference, Austin, TX, pp. 131–146 (1993).

* cited by examiner

Primary Examiner—Christopher R. Tate
(74) Attorney, Agent, or Firm—Browdy and Neimark

(57) ABSTRACT

A microbial consortium, ATCC 202177, is enriched to remove target sulfur compounds from gases in the presence of ammonia, cyanide, carbon monoxide, and other toxic gases and mixtures thereof. The ATCC 202177 consortium is cultured in an anaerobic or aerobic nutrient medium until enough cells of ATCC 202177 are recovered to remove the target sulfur species at a pressure ranging from 1 to 80 atmospheres.

14 Claims, 12 Drawing Sheets

Figure 4A
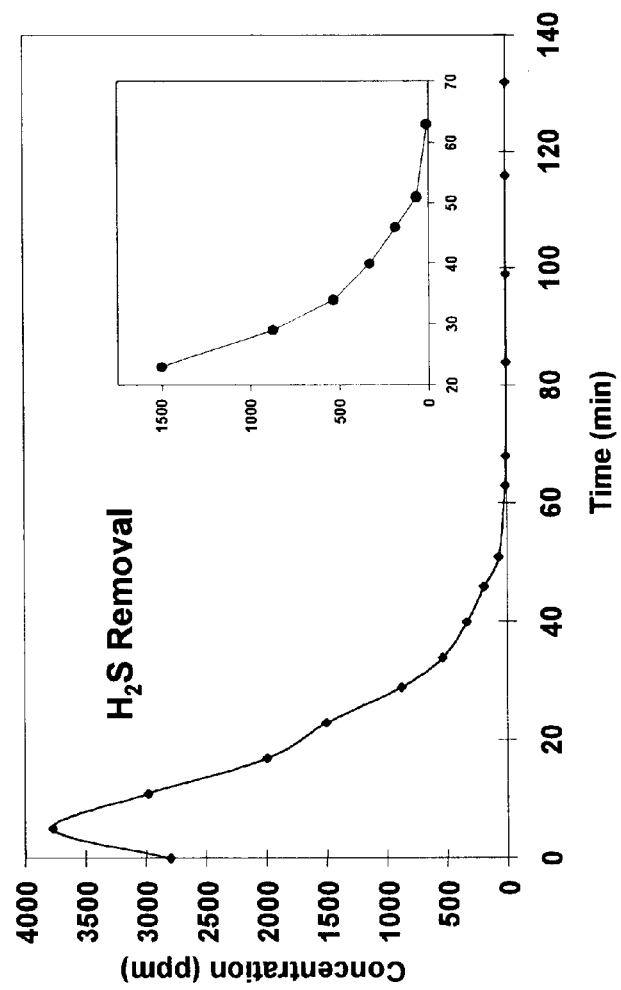
Panel B
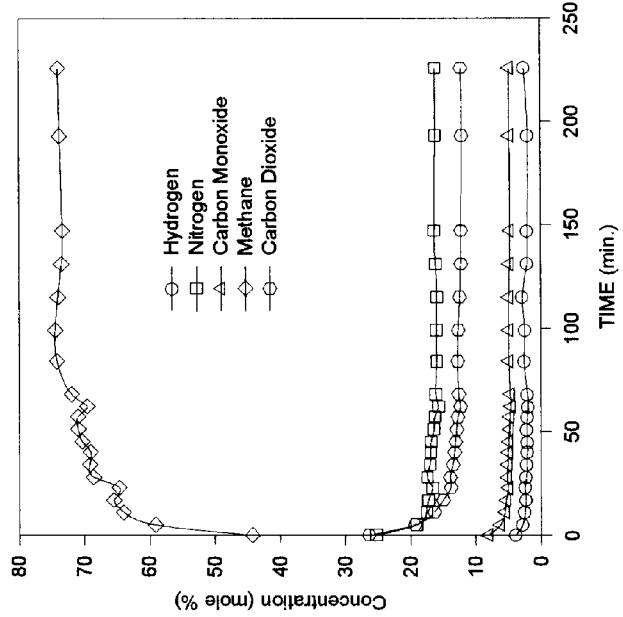
Panel A

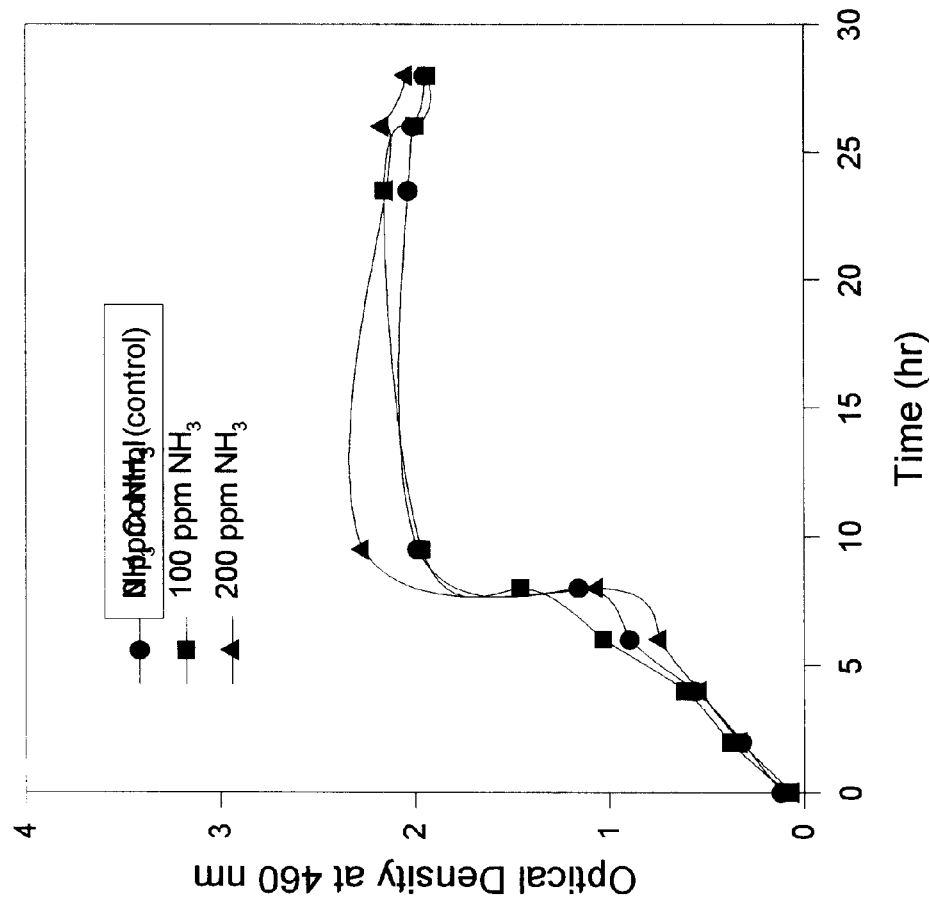

MICROBIOLOGICAL DESULFURIZATION OF SULFUR CONTAINING GASES

CROSS-REFERENCE TO RELATED APPLICATIONS

This application is a continuation-in-part of application Ser. No. 08/651,793, filed May 20, 1996, now U.S. Pat. No. 5,981,266, the entire contents of which are hereby incorporated by reference.

FIELD OF THE INVENTION

The present invention relates to a biocatalyst which improves microbiological desulfurization of sulfur containing gases.

BACKGROUND OF THE INVENTION

Natural and other gases, such as landfill gas, syngas, and geothermal gas, in the United States often contain hydrogen sulfide as a major contaminant. Hydrogen sulfide is a toxic, acid gas that is corrosive in the presence of water. A significant portion of the gas produced in the U.S. does not meet pipeline standards and requires treatment to reduce the concentration of hydrogen sulfide to ¼ grain per 100 standard cubic feet or ≦4 ppm on a volume basis. Other sulfur compounds which may occur in these gases include carbonyl sulfide, carbon disulfide, and mercaptans, such as dimethyl mercaptan, methyl mercaptan, and ethyl mercaptan. While sulfur dioxide is occasionally present, sulfur dioxide is not one of the common contaminants in these gases.

Conventional commercial processes for removing gaseous sulfur species from a given gas stream are based upon using at least two groups of chemicals. One group is amine-based reagents, while the second group comprises liquid redox reagents. Both groups of chemicals need to be regenerated using additional process steps. Another limitation of these processes is that they are not cost effective at low throughput (amine, less than 100 million standard cubic feet per day, or <100 MMSCFD, and liquid redox at <5 MMSCFD) of the contaminated gases. Still other limitations are related to the operation of a gas-processing plant when chemical reagents, such as a liquid redox catalyst, are used.

Another group of chemical reagents, called Scavengers can be used for low-volume gas production facilities. The limitations, however, include (i) only one-time throughput of the reagent, (ii) high cost of the reagents, and (iii) production of hazardous wastes that require costly disposal.

Biological processes can overcome the limitations of processes based on chemical reagents. Commonly known biological processes are of two types. In the first type, a chemical reagent, such as LO-CAT catalyst, which principally comprises chelated iron sulfate, oxidizes hydrogen sulfide to elemental sulfur. Subsequently, the spent catalyst is regenerated using microorganisms, such as *Thiobacillus ferrooxidans*, rather than air oxidation. In this way, the process is much safer and the power requirements are reduced, resulting in a more economical overall process.

These microorganisms carry out the regeneration of the LO-CAT catalyst according to the following reaction:

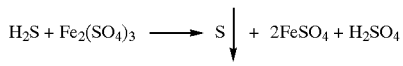
(i)

(ii)

A recent patent to Rai, U.S. Pat. No. 5,508,014, teaches that the microorganism *Thiobacillus ferrooxidans* regenerates the LO-CAT catalysts at much higher rates than can be achieved through air oxidation.

The second type of biological process is the direct treat process, in which bacteria oxidize the sulfur species by using the sulfur species as an energy source. This reaction is carried out in the presence of the following components:

a terminal electron acceptor such as $NO_3^{-1}$;

a source of carbon, such as carbon dioxide, present in the gas stream, or $HCO_3^{-1}$, present in the nutrient solution (culture medium) for the growth of bacteria; and $NH_4^{+1}$ as a source of reduced nitrogen.

The predominant biochemical reaction underlying the direct treat biological process is as follows:

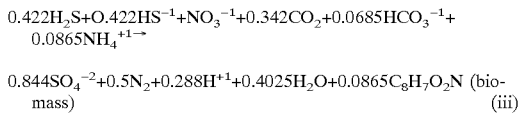
(iii)

There are a number of chemolithotrophic bacteria that oxidize elemental sulfur and use reduced or partially reduced sulfur compounds as an energy source, carbon dioxide or bicarbonate as a carbon source, and ammonium ion as a source of reduced nitrogen. For example, the anaerobic photosynthetic bacterium *Chlorobium thiosulfatophilum* is used to convert sulfides to sulfate (Cork et al, 1982). Since the process must be conducted under photosynthetic conditions, the capital and operating costs for this process are economically unattractive.

Another commonly known chemolithotrophic microorganism is the aerobic bacterium *Thiobacillus denitrificans*. One process for desulfurizing sour natural gas using this bacterium is disclosed in Sublette, U.S. Pat. No. 4,760,027. This patent describes a process wherein bacteria of the Thiobacillus genus convert sulfides to sulfates under aerobic conditions and at a controlled temperature of about 30° C.

A review of the literature, however, reveals that, in contrast to a homogeneous culture consisting of only one bacterial species (e.g., *Thiobacillus ferrooxidans* or *T. denitrificans*), a mixed microbial culture (consortium) composed of compatible bacteria or microorganisms of different biochemical and morpho-physiotypes working in synergy bring about 75% higher sulfide oxidation than a chemical agent. The important condition, nevertheless, is that in this system the sulfide concentration should be ≦3–8 mM and reaction conditions should be favorable for the microbial metabolism.

The above-described direct treat microbial process for direct removal of hydrogen sulfide from methane or fuel gas streams containing other hydrocarbons, however, poses a potential danger of explosion when, for example, methane and air are mixed. ARCTECH has developed an anaerobic, non-photosynthetic biological process, described in application Ser. No. 08/651,793, in which a microbial consortium, SSII (also known as ATCC 202177) from ARCTECH's Microbial Culture Collection (AMCC) reduces the hydrogen sulfide concentration from up to 10,000 ppm to less than 4 ppm. The SSII microbial consortium was deposited in the American Type Culture Collection (ATCC) on Oct. 6, 1998 with the ATCC Patent Depository. The ATCC is located at 10801 University Blvd., Manassas, Va. 20110. The deposit number of the SSII microbial consortium is ATCC 202177. ATCC 202177 oxidizes hydrogen sulfide to elemental sulfur, which is neither corrosive nor toxic.

There is a critical need for a cost-effective system for removing gaseous sulfur species in the presence of other gases, even in small-volume operations. It is critical, then, to minimize chemicals and nutrients, produce useful by-products which are not hazardous, and eliminate a separate regeneration step of the catalyst.

The present invention is related to a method for preparing and enhancing the ability of ATCC 202177, also known as SSII or DSC2, used in the parent application to remove hydrogen sulfur at high rates. Specifically, the present invention is related to a preparation of ATCC 202177 which is designed to remove carbon dioxide and gaseous sulfur species, such as hydrogen sulfide, carbon disulfide, and mercaptans, in the presence of methane, hydrogen, carbon monoxide, and other gases.

SUMMARY OF THE INVENTION

It is an object of the present invention to overcome the deficiencies in the prior art.

It is another object of the present invention to provide a microbial consortium that can metabolize sulfur under anaerobic conditions.

It is another object of the present invention to provide a microbial consortium which is capable of reproducible sulfur removal, under anaerobic conditions, in the presence of a gas stream, such as methane or other hydrocarbons, hydrogen, syngas, biogas, geothermal gas, landfill gas, tail gas, and the like.

It is a further object of the present invention to provide a method for the production of a facultative anaerobic microbial consortium which is capable of reproducibly removing gaseous sulfur species when these sulfur species are contaminants in a gas stream containing any one, or all of the following: ammonia, carbon dioxide, carbon monoxide, cyanide, hydrogen, methane, higher gaseous hydrocarbons, and nitrogen.

It is still another object of the present invention to provide a process for anaerobic microbial desulfurization of a given gas stream in the presence of ammonia, carbon dioxide, carbon monoxide, cyanides, hydrogen, methane, aliphatic hydrocarbons, and nitrogen.

The above objectives are achieved herein by providing a viable mixed culture, or consortium, of microorganisms, which has been deposited under the Budapest Treaty with the American Type Culture Collection (ATCC) as deposit number ATCC 202177. This microbial consortium, known as ATCC 202177 or SSII, is prepared by enriching microorganisms in the presence of target gaseous sulfur species contained in the presence of ammonia, carbon monoxide, carbon dioxide, cyanide, hydrogen, and nitrogen.

The microorganisms are obtained from a variety of waters from a number of different ecological niches. These niches include ecological streams, such as acid mine drainage or wastewater plants which process a variety of industrial wastewaters. The water from these niches is suspended in a nutrient medium for the growth of the microorganisms present in the waters. The headspace gas of the culture vessels (bioreactors) used for growing the microorganisms contains a mixture of gaseous sulfur compounds, such as hydrogen sulfide, carbon disulfide, carbonyl sulfide, dimethyl, methyl, and ethyl mercaptans, in the presence of carbon dioxide and nitrogen. During the enrichment process, the pH of the growth medium is maintained near neutral, and the temperature is maintained in a range of 10–60° C.

The ATCC 202177 consortium was subsequently evaluated for its ability to remove gaseous sulfur compounds, such as hydrogen sulfide, carbon disulfide, carbonyl sulfide, dimethyl, methyl, and ethyl mercaptans, either as single components or as mixtures of two or more of these compounds. The gaseous sulfur compounds were mixed with a gas stream containing at least one of the following gases: ammonia, carbon monoxide, carbon dioxide, hydrogen, methane, and nitrogen.

The reaction mixture can also contain cyanide, either in the gas or liquid phase. The ATCC 202177 is suspended in its nutrient medium (TSN, Table 1), and under anaerobic conditions in an appropriate culture vessel. Under these conditions, the ATCC 202177 is contacted with the gaseous mixture containing sulfur compounds along with other gases, including ammonia and cyanide(s). The latter two compounds can be either in the liquid or the gas phase. The exit gas stream from the culture vessel (a bioreactor) is free of gaseous sulfur compounds, particularly hydrogen sulfide.

TABLE 1

Composition of TSN Medium

| Component | Quantity/L |
|---|---|
| $Na_2HPO_4$ | 1.2 g |
| $KH_2PO_4$ | 1.8 g |
| $MgSO_4 \cdot 7H_2O$ | 0.4 g |
| $NH_4Cl$ | 0.5 g |
| $CaCl_2$ | 0.03 g |
| $FeCl_3$ | 0.02 g |
| $MnSO_4$ | 0.02 g |
| $Na_2S_2O_3$ | 10.0 g |
| $NaHCO_3$ | 1.0 g |
| $KNO_3$ | 5.0 g |

The reactor may be operated at a temperature ranging from about 10–60° C.

BRIEF DESCRIPTION OF THE DRAWINGS

FIG. 4A is a graph illustrating how enriched ATCC 202177 removes hydrogen sulfide in a gaseous mixture without affecting other components of the gas mixture.

FIG. 5 illustrates that enriched ATCC 202177 is not inhibited by up to 200 ppm ammonia.

DETAILED DESCRIPTION OF THE INVENTION

The microbial consortium of the present invention, ATCC 202177, was developed from samples obtained from sewage sludge, acid mine water, and other such resources. Enrichment cultures were prepared by inoculating the samples at 20% loading (volume into volume) into serum vials or bottles of 125-mL containing 50 mL of TSN. In the TSN of the present invention, sodium thiosulfate is the sole source of sulfur, and 0.12% yeast extract, or commercially available Sheftone™ products or Cargill 200/20 as the organic nitrogen supplement. Replacement of yeast extract with Sheftone™ products (an organic nitrogen source obtained from Sheffields Products of Detroit, Mich.) or Cargill 200/20 as the organic nitrogen source and incorporating any one of the latter products into TSN did not compromise the removal of gaseous sulfur species. The abiotic controls did not contain any microbial inoculum, but contained the same volume of sterile water prepared under anaerobic conditions. After inoculation, the bottles were incubated on a shaker incubator oscillating at 200 rpm maintained at 25° C., to 30° C. (77° F. to 86° F.) or at a temperature of 60° C. (140° F.).

The microbial growth in the bottles was monitored by measuring the absorbance of the culture liquid at 460 nm and also by direct microscopic counts of the culture liquid. These measurements were performed on samples collected at periodic intervals by withdrawing the culture liquid from the bottles or serum vials. The direct microscope counts were conducted to ensure the microbial growth because, as one skilled in the art is aware, sometimes the turbidity of the nutrient medium can increase because of the products of microbial metabolism, rather than solely from microbial multiplication.

Subsequently, the cultures showing appreciable growth in the presence of the target gaseous contaminants were transferred into fresh TSN for at least three passages to ensure that the cultures were growing. The culture that grew most rapidly and showed the highest growth was designated SSII, and is also known as DSC2. After verifying all its properties as described herein, this culture was deposited with ATCC as accession number ATCC 202177.

The ATCC 202177 was then inoculated at 20% v/v loading in 125 mL serum vials containing 50 mL of TSN and cultivated for 24 hours at 25–30° C. (77–86° F.) in a shaker incubator. Subsequently, the ATCC 202177 was inoculated at 10% v/v loading in 500 mL of fresh TSN contained in a one-liter Wheaton bottle. The surviving ATCC 202177 was always maintained in 500 mL TSN and, whenever necessary, was cultivated in 500 mL TSN for 24 hours to yield sufficient ATCC 202177 biomass to be loaded at a minimum of 1% wet cell weight to total TSN volume, or in the range of 1–20% biomass. These loadings were used in the experiments described below, which illustrate the characteristics of ATCC 202177.

Figure 1:
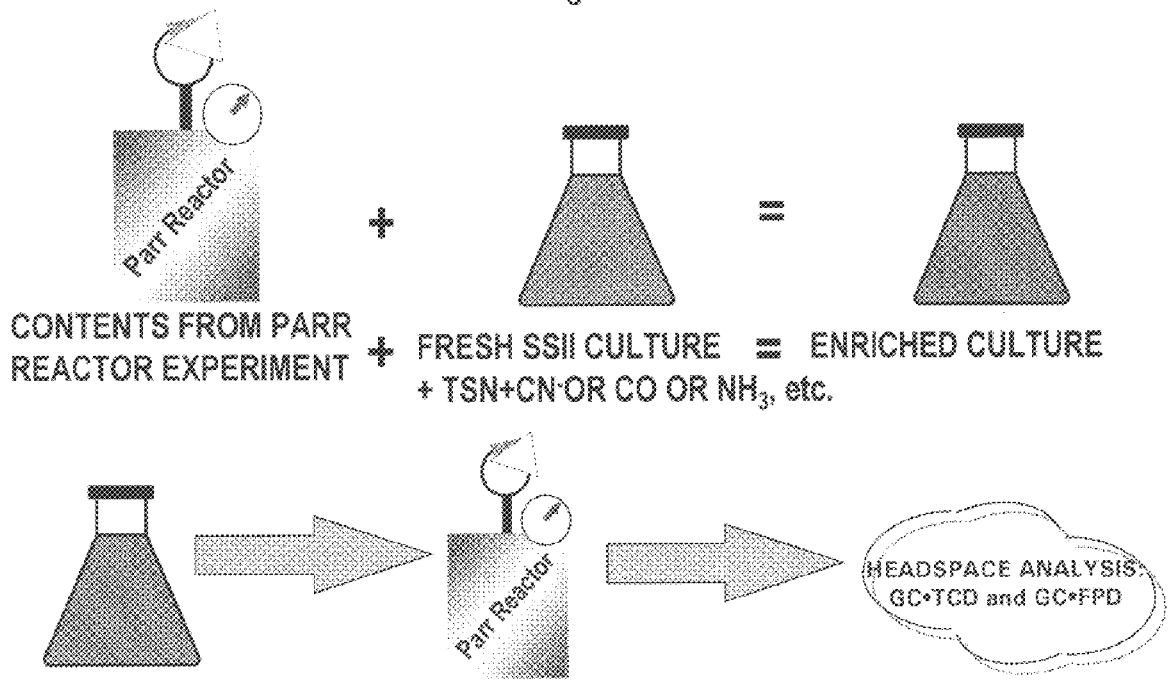
FIG. 1 is a flow diagram illustrating the method of culturing ATCC 202177 according to the present invention.

The method for preparing ATCC 202177 is summarized in FIG. 1. General experimental procedures used are detailed below.

General Experimental Procedures

Initially, all experimental procedures to handle the microbial cultures were conducted under anaerobic conditions according to the techniques described by Hungate as modified by Bryant. An anaerobic glove box (Coy Corporation, Ann Arbor, Mich.) was used for culture transfers, cell washing, and isolation of cell types in microbial consortium. In the glove box, anaerobic conditions were maintained with an oxygen-free mixture of nitrogen plus hydrogen (95.5:4.5). The anaerobic conditions during preparation of TSN and in the reaction vessels were maintained by bubbling an oxygen-free mixture of nitrogen and carbon dioxide (80:20). For these experiments, all solutions, reagents, and culture media were also prepared under the same anaerobic conditions.

The composition of the culture medium called thiosulfate nutrient (TSN) medium to grow ATCC 202177 is given in Table 1 above. As one skilled in the art of practiciing anaerobic microbiology would appreciate, the TSN was prepared by stepwise addition of each one of the components of the TSN. Addition was such that the compound added previously was completely dissolved before the next one was added to the boiling water. The boiling water was stirred constantly and simultaneously purged with a mixture of oxygen-free nitrogen and carbon dioxide (80:20). After all of the components of TSN were dissolved, the TSN was cooled under constant stirring and simultaneous purging with a mixture of oxygen-free nitrogen and carbon dioxide (80:20) to room temperature. Subsequently, the pH of the TSN medium was adjusted to 7.5, still under purging. Then, under purging, 50 mL aliquots of TSN were transferred to 125-mL serum vials. Larger quantities, up to 500 mL, were transferred to one liter-Wheaton bottles. The vials were stoppered with butyl rubber stoppers and aluminum crimp sealed. The Wheaton bottles were butyl rubber stoppered and screw capped. Then the serum vials and Wheaton bottles were sterilized at 121° C. and 15 psi for 20 minutes. After cooling, the serum vials were used for initial screening experiments. The Wheaton bottles were used for growing the microbial inocula.

For any given experiment, in any type of culture vessel, the efficacy of the ATCC 202177 to remove the target gaseous sulfur compounds contained in a given gas stream was evaluated by analyzing the headspace of the reaction vessel. One skilled in the art would realize that the headspace of a vessel is the space between the bottom of the cover (butyl rubber stopper for serum vials, stainless steel flange cover for the Bioflow and Parr reactors) of a reactor, and the top of the liquid meniscus in the vessel. In this reaction vessel, ATCC 202177 was cultivated as submerged culture in the TSN. The headspace gas was sampled at periodic intervals (every 5 minutes of up to one hour; every half hour thereafter up to four hours, to at least once every 24 hours) with a gas tight syringe. During the preliminary experiments, liquid samples were also aseptically and anaerobically removed for analysis of pH, cellular protein (to measure cell growth), and estimation of soluble sulfur species: elemental sulfur ($S_0$), $SO_3^{-2}$, $SO_4^{-2}$, $S_2O_3^{-2}$, and $S^{-2}$.

The above procedures were used because ATCC 202177 was originally developed under anaerobic conditions. Since anaerobic cultures require special attention and techniques, an experiment was set up to determine whether ATCC 202177 is a facultative or obligate anaerobe. The consortium was found to be composed of microaerophilic or facultative anaerobic microorganisms. Therefore, henceforth the cultures were treated in ambient conditions. The anaerobic methods, however, were continued to maintain the ATCC 202177. Additionally, the experiments to evaluate removal of sulfur species were carried out under anaerobic conditions.

Analytical Methods

The microbial load and the growth were determined either by direct cell count, measuring the absorbance at 460 nm (OD460) or by wet and dry cell weight.

The wet cell weight was determined on a 24–48 hour culture of the test organism. The culture was dispensed in a pre-weighed centrifuge bottle of 25 to 250-mL. The cultures were harvested through centrifugation at 3000 to 3500 rpm for 20 minutes Subsequently, the cell pellet was washed with Tris-HCl buffer (50 mM, pH 7.5) through resuspension and centrifugation. Finally, the centrifuge bottle containing the cell pellet was weighed. For determining the dry cell weight, the cell pellet after determining the wet weight was resuspended in 50 mL of Tris-HCl buffer (50 mM, pH 7.5) and transferred to a pre-weighed aluminum boat. Three such preparations were used for this determination. In three other pre-weighed boats, 50 mL Tris-HCl (50 mM, pH 7.5) was dispensed into each one. These three boats served as controls. All six boats were then incubated at 105° C. for 16 hours. Subsequently, the boats were cooled in a desiccator and weighed until a constant weight was obtained. The wet weight (wwt) was obtained as:

$$wwt = A - B$$

where A is the weight of the harvested, washed cell pellet plus the pre-weighed centrifuge bottle; and B is the weight of the centrifuge bottle.

Similarly, the dry weight (dwt) was calculated from the formula:

$$dwt = C - D$$

where C is the weight of the dried, pre-weighed aluminum boats containing 50 mL of the washed culture suspension in the Tris-HCl buffer, and D is the weight of the dried, pre-weighed aluminum boats containing 50 mL of the Tris-HCl buffer.

Determination of Headspace Gases

Headspace gas analyses were conducted by directly introducing the needle of a pressure-tight gas syringe into the butyl rubber stoppers on the sample containers. For initial experiments in serum vials, prior to sampling for headspace gas, the pressure-tight syringe was made anaerobic by flushing it three times with an oxygen-free nitrogen:carbon dioxide mixture (80:20). For later experiments, however, this flushing step was not used because by then it was known that the ATCC 202177 consortium is a facultative anaerobe/microaerophilic organism.

Headspace gas composition of carbon dioxide, carbon monoxide, hydrogen, methane, and nitrogen was determined by gas chromatography using a thermal conductivity detector (TCD). A GOW-MAC gas chromatograph (GC) fitted with a 10×18 inch OD stainless steel column packed with 100/120 mesh Carbosieve S-II (Supelco Co.) was used to analyze the gas samples. The conditions were: column temperature, 200° C.; detector and injector temperatures, 220° C.; detector current, 170 mA. Helium was used as a carrier gas (30 mL/min at 50 psi on the cylinder). A HP integrator (Model 3396A) integrated the data. The calibration standard was prepared with a mixture of carbon dioxide (29.3%), carbon monoxide (10.2%), hydrogen (4.9%), nitrogen (24.9%), and methane (30.7%).

A Varian model 3700 gas chromatograph was used to analyze the gaseous sulfur species. A flame photometric detector with sulfur filter at 220° C. was used. The carrier gas was helium at a flow rate of 40 mL/min. A 60/80 Carbopak B, 1.5% XE-60, 1% $H_3PO_4$ glass column was used. The oven temperature was isothermal at 50° C., and the injector was set at 220° C. This instrument was also calibrated with a standard gas mixture consisting of 10 and 1000 ppm hydrogen sulfide and 999 ppm each of carbonyl sulfide, carbon disulfide, methyl mercaptan, ethyl mercaptan, and dimethyl mercaptan.

The fate of major ionic species comprising the culture medium was monitored by high-pressure liquid chromatography (HPLC) and inductively coupled plasma spectrometer (ICP-AES). The ions monitored were $NH_4^{+1}$, $Fe^{2+}$, $Na^{+1}$, $K^{+1}$, $Mg^{2+}$, $Mn^{2+}$, $Zn^{2+}$, $NO_2^{-1}$, $NO_3^{-1}$, $S^{-2}$, $SO_3^{-2}$, $SO_4^{-2}$, and $S_2O_3^{-2}$. The parameters used for HPLC were a Waters 501 HPLC pump connected to a WISP U6K autosampler. The columns used were IC-PAK anion HC and Hamilton PRP-X200. The detectors used were a 400 UV detector and a 430 conductivity detector. Different eluents were used depending on the ion to be analyzed. For example, 5 mM dibasic sodium phosphate was used to separate sulphur species. The eluent was prepared by adding 0.7092 g dibasic sodium phosphate to a one-liter volumetric flask and bringing the volume to the mark with HPLC grade water. The eluent was filtered through a 0.2 μm membrane filter, and protected from adsorbing atmospheric carbon dioxide.

Standard solutions for HPLC were prepared by standard methods well known to those skilled in the art.

Inoculum Preparation

For all the following examples, the inoculum of ATCC 202177 was prepared according to the following procedure. For initial screening experiments, the inocula were prepared in one-liter Wheaton bottles containing 300 mL of the TSN medium. After an incubation period of one week, the cultures were aseptically and anaerobically harvested by centrifugation and washed twice in an equivalent quantity of 50 mM, pH 7.5 Tris-HCl buffer, by re-suspension and centrifugation. Finally, the washed microbial pellet was re-suspended in sufficient TSN medium to provide enough inoculum for the experiment to be performed. Initial screening experiments were carried out at a microbial loading of 1%. The wet weight of the inoculum was recorded and the total cell count measured directly with epifluorescence microscopy. This method of inoculum monitoring provided a means of keeping the initial bacterial inoculum constant for different treatments within a given experiment or between the experiments. It also provided a method whereby all the experiments could be carried out at a consistent microbial load. Thus, any discrepancy due to variations in the microbial loading could be disregarded or minimized.

Larger quantities of inoculum required for scaled up experiments were prepared in four-liter Erlenmeyer flasks containing two liters of TSN. After an appropriate period of incubation, the biomass was harvested by centrifugation, washed with Tris-HCl buffer (50 mM, pH 7.5) for two passages, and re-suspended at appropriate biomass loading. The biomass loading depended upon the experiment to be conducted and the reactor to be used for that experiment. For example, 2.1 g wet biomass was loaded in 600 mL TSN to obtain 0.35% microbial loading.

EXAMPLES

The following examples will familiarize one skilled in the art with the present invention. These examples are illustrative and are not meant to limit the scope of the invention in any way.

Example 1

Isolation of Individual Microbial Types Constituting ATCC 202177

1 mL aliquots of an actively grown inoculum were aseptically added to sterile tubes containing 9 mL of 0.1% peptone water. The dilution was $10^1$/mL. Subsequent dilutions in the range of $10^{-2}$ to $10^{-9}$/mL were prepared by aseptically withdrawing 1 mL aliquots from tubes 1 through 8 and adding this to tubes 2 through 9. Each of tubes between tubes 2 and 9 also contained 9 mL of 0.1% peptone water. Then, 0.1 mL aliquots of the contents of tubes 4, 6, and 9 were transferred to aseptically prepared plastic petri plates containing TSN+2% agar (to solidify the TSN). Thus, the final dilutions ranged from approximately $10^{-6}$/mL to $10^{-10}$/mL. These plates were subsequently incubated in a sterile, moist chamber for up to one week at room temperature. After this time five morphologically distinct colonies were observed on each of the plates. Each of the distinctive colonies was re-plated, one colony to a plate to ensure homogeneity of the colony, i.e., the colonies looked the same as on the original plate. These colonies were then examined microscopically under phase contrast at 1000 magnification to ensure that each colony consisted of only one morphotypic bacterium.

The morphological characteristics of ATCC 202177 and of the five microorganisms constituting ATCC 202177 are described below in Table 2.

TABLE 2

Morphological Characteristics of Isolates of SSII (ATCC 202177)

| Isolate Name | Colony Morphology | Size and Shape |
| --- | --- | --- |
| Isolate A | round, entire, creamy with yellowish center, raised and mucoid colony about 2 mm in diameter | gram negative bacilli, 2.5 to 3.0 μm long and 0.8 to 1 μm wide |
| Isolate B | round, entire, creamy, raised and mucoid colony about 2 mm in diameter | gram negative bacilli, 1.6 to 1.9 μm long and 0.4 to 0.5 μm wide |
| Isolate C | round, entire, creamy, raised and mucoid colony about 1 mm in diameter | gram negative bacilli, 1.6 to 1.9 μm long and 0.8 to 1 μm wide |
| Isolate D | irregular, serrated, creamy, flat and non-mucoid about 4 mm in diameter | gram negative bacilli, 2.5 to 3.0 μm long and 0.8 to 1 μm wide |
| Isolate E | round, yellowish, entire, raised and mucoid about 1 mm in diameter | gram negative bacilli, 1.6 to 1.9 μm long and 0.4 to 0.5 μm wide |

*The isolates were plated on TSN medium with 2% Agar.

Example 2

Comparative Hydrogen Sulfide Removal at High Pressure by ATCC 202177 and Different Bacterial Isolates Constituting ATCC 202177

Starting from 1% wet cell loading, e.g., 10 g/L of the TSN, each of the isolates and ATCC 202177 were grown for approximately two weeks to obtain approximately 60 grams wet cell weight for each of the six microorganisms. In separate experimental runs, 60 grams wet cell weight of each of ATCC 202177 and each of the isolates comprising ATCC 202177 were evaluated for removal of hydrogen sulfide from a gaseous mixture. The experiments were run in a Parr reactor at 1000 psi (68.03 atm) and 60° C. according to the schematic shown in FIG. 2. The data collected on residual hydrogen sulfide gas in the culture vessel over a period of time was used to calculate the removal rates of hydrogen sulfide. The data shown in Table 3 indicate that all of the constituent isolates making up ATCC 202177 are necessary to obtain high removal rates of hydrogen sulfide.

TABLE 3

Comparative Removal of $H_2S$ by the ATCC 202177 and Each of Its Constituting Bacterial Isolates*
Experimental Conditions:
Batch Mode at 1,000 psi (68.03 atmospheres), pH 7.5 and 60° C.

| | $H_2S$ Concentration (ppmv) | | |
| --- | --- | --- | --- |
| Organism | Inlet | Outlet | $H_2S$ Removed % |
| Control without bacteria | 3,900 | 2,250 | 42.31 |
| ATCC 202177 | 3,000 | 0 | 100.00 |
| Isolate A | 3,900 | 625 | 83.97 |
| Isolate B | 4,000 | 1,500 | 62.50 |
| Isolate C | 3,000 | 250 | 91.70 |
| Isolate D | 4,250 | 2,500 | 41.18 |
| Isolate E | ND | ND | ND |

Example 3

Comparative Hydrogen Sulfide Removal by ATCC 202177 and Its Isolates at Atmospheric Pressure The experiment of Example 2 was conducted at atmospheric pressure. In this experiment, the gas from a single source was simultaneously fed to several different one-liter vessels, each containing 0.6 liters of TSN medium. Each vessel contained either ATCC 202177 or one of the isolates making up ATCC 202177. The control was TSN without any bacteria. In this example, the gas stream containing the gaseous sulfur species was bubbled through the vessels at 1.8 liter/hour. The removal of hydrogen sulfide was again monitored by analyzing headspace gas and continued until a steady state was reached. After the steady state was achieved, the removal was monitored for two to three hours. These data, shown in Table 4, again indicate that each one of the isolates of ATCC 202177 is required for a higher removal of hydrogen sulfide from a gas stream contaminated with sulfur compounds.

TABLE 4

Comparative Removal of $H_2S$ by the ATCC 202177 and Each of Its Constituting Bacterial Isolates*
Experimental Conditions:
Continuous Mode at Ambient Pressure

| Treatment | $H_2S$ Concentration (ppmv) | | |
| --- | --- | --- | --- |
| (Organism/Control) | Inlet | Outlet | $H_2S$ Removed % |
| Control without bacteria | 200 | 16.6 | 91.70 |
| ATCC 202177 | 200 | 0.0 | 99.97 |
| Isolate A | 200 | 3.2 | 98.40 |
| Isolate B | 200 | 3.0 | 98.50 |
| Isolate C | 200 | 2.9 | 98.60 |
| Isolate D | 200 | 7.3 | 96.30 |
| Isolate E | 200 | 3.9 | 98.05 |

Examples 2 and 3 clearly establish that ATCC 202177 can remove hydrogen sulfide when carbon dioxide, methane, and nitrogen are present in the gas mixture.

The next examples were used to evaluate the removal of hydrogen sulfide in the presence of carbon dioxide, methane, nitrogen, and other compounds that are present in either the gas or the liquid phase of the reaction mixture. The compounds tested were: carbon monoxide (CO), hydrogen ($H_2$), cyanide (CN), and ammonia ($NH_3$).

Example 4

Figure 2:
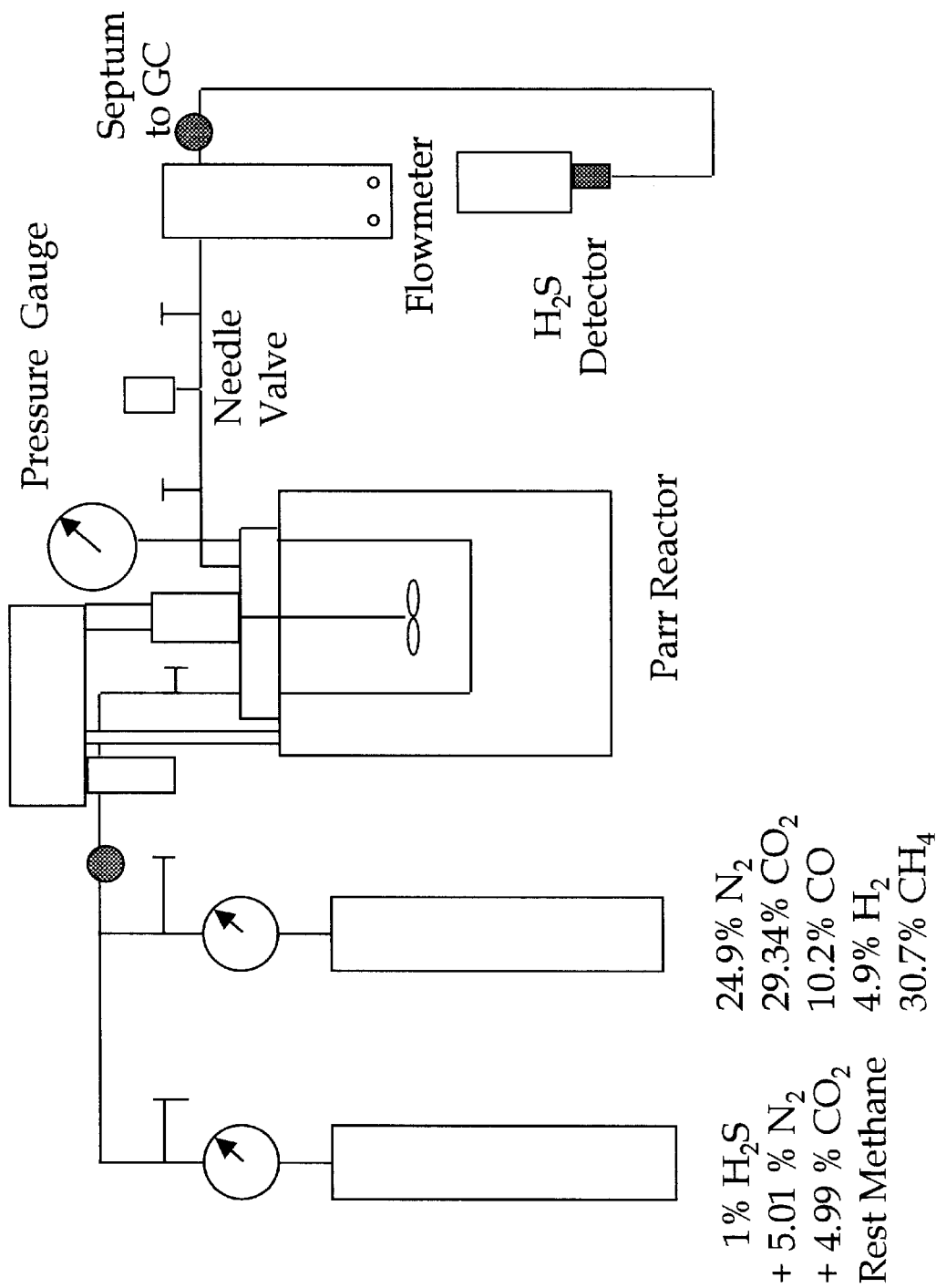
FIG. 2 is a flow diagram illustrating how ATCC 202177 removes sulfur species from a gas mixture.

Removal of Hydrogen Sulfide in the Presence of Carbon Monoxide, Carbon Dioxide, Hydrogen, Methane, and Nitrogen The experimental setup for Examples 4–7 was that shown in FIG. 2. The following gives the general experimental procedure used to evaluate the efficacy of ATCC 202177 in removing hydrogen sulfide in the presence of carbon monoxide, cyanide, and ammonia.

For these experiments, 600 mL of TSN medium was inoculated with 10% (w/v) wet cells of ATCC 202177 and the culture vessel was incubated for sixteen hours at room temperature (approximately 20–23° C.) under constant agitation. One hour prior to the experiment, the culture was supplemented with 1.2 g of organic nitrogen supplement and 6 g of sodium thiosulfate. This culture was then charged into the Parr reactor, and the reaction mixture was allowed to come to 37° C. At this point the Parr reactor was pressurized to 68.03 atm with the following gas mixtures:

TABLE 5

| To 34.01 atm with Gas Mixture A | To Additional 34.01 atm with Gas Mixture B |
|---|---|
| 29.34% Carbon Dioxide | 4.99% Carbon Dioxide |
| 10.2% Carbon Monoxide | 1% Hydrogen Sulfide |
| 4.9% Hydrogen | 89% Methane |
| 30.7% Methane | 5.01% Nitrogen |
| 24.9% Nitrogen | |

After pressurizing the Parr reactor, the headspace gas was analyzed for carbon dioxide, carbon monoxide, hydrogen, hydrogen sulfide, methane, and nitrogen. The headspace of the Parr reactor was sampled soon after pressurization (time zero) and subsequently at intervals of ten minutes for the first hour and thereafter at 15 minute intervals for two hours, and finally at one hour intervals for the duration of the experiment. The data collected showed that under the experimental conditions used, hydrogen sulfide was not removed by ATCC 202177.

Example 5

Preparation of ATCC 202177 Capable of Removing Hydrogen Sulfide in the Presence of Carbon Monoxide, Carbon Dioxide, Hydrogen, Methane, and Nitrogen Before evaluating the removal of hydrogen sulfide in the Parr reactor any further, the growth capability of ATCC 202177 in the presence of carbon monoxide and hydrogen in the gas mixture was evaluated. This experiment was conducted in three sets of three serum vials each, for a total of nine serum vials. The serum vials were distributed as follows.

Set one comprised three 125-mL serum vials containing 50 mL TSN medium prepared anaerobically as described in the general experimental procedures. The headspace of these vials was exchanged with a gas mixture of the following composition: carbon dioxide, 29.34%; carbon monoxide, 10.2%; hydrogen, 4.9%; methane, 30.7%; and nitrogen, 24.9%.

Sets two and three each, also comprised three 125-mL serum vials containing 50 mL TSN medium prepared anaerobically as described above. The headspace of these vials was not exchanged with the above gas mixture.

Sets one and two were charged at 10% biomass loading with a freshly prepared culture of ATCC 202177. Thus, set two was a biotic control for set one. Set three served as an abiotic control for both sets one and two. All of the vials were incubated at 23–25° C. in a shaker incubator oscillating at 100 rpm. At the beginning of the experiment and at predetermined periodic intervals, liquid samples were taken from all nine vials and were monitored for turbidity at 460 nm. The data show that the ATCC 202177 did not exhibit any significant growth.

Figure 3:
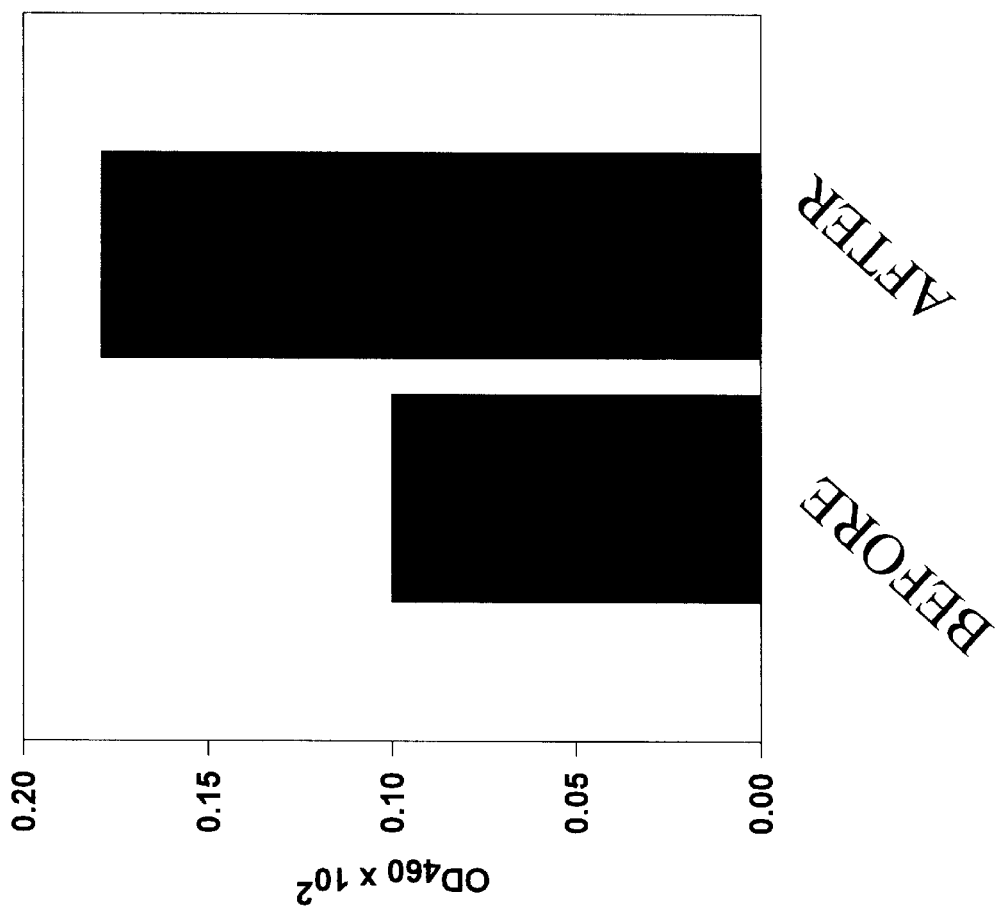
FIG. 3 is a graph illustrating that ATCC 202177 was enriched to grow in the presence of a mixture of carbon dioxide, carbon monoxide, hydrogen, methane, and nitrogen.

Further development of ATCC 202177 involved incubating a mixture of ATCC 202177 obtained from the Parr reactor mixed with a freshly-prepared culture of ATCC 202177 at a biomass loading of 10% in 50 mL of TSN in a serum vial. The headspace of the serum vial contained the gas mixture composed of: carbon dioxide, 29.34%; carbon monoxide, 10.2%; hydrogen, 4.9%; methane, 30.7%; and nitrogen, 24.9%. This step was continued for three transfers. Then the growth of ATCC 202177 was re-examined in the vials prepared as above. The data shown in FIG. 3 exhibit an increase in the growth of the enriched ATCC 202177 compared to what was observed with un-enriched ATCC 202177.

Figure 4B:
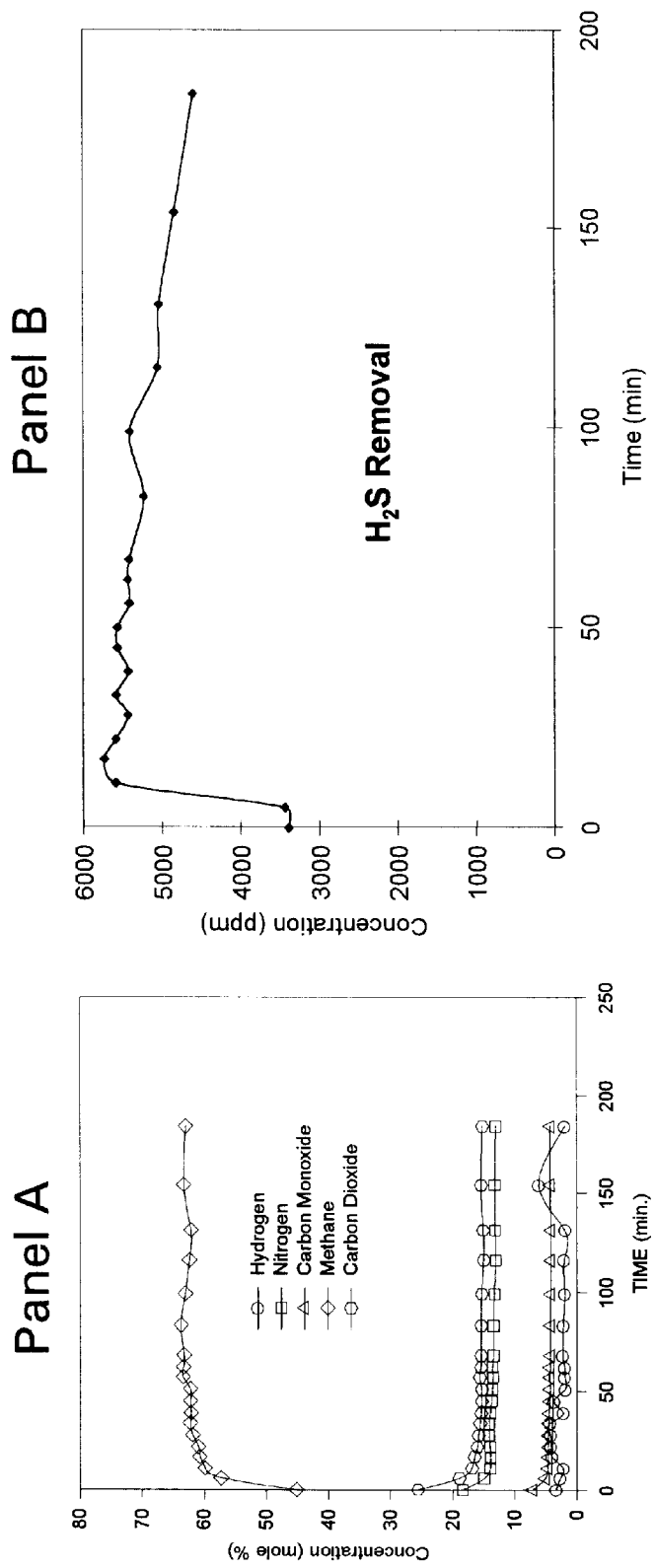
FIG. 4B is a graph illustrating how hydrogen sulfide in a gaseous mixture is removed in the absence of ATCC 202177.

The experiment of Example 4 was repeated with enriched ATCC 202177 as prepared above. An abiotic control experiment was also run in a similar manner. The data show that there was little hydrogen sulfide removal in the absence of ATCC 202177 (FIG. 4A) in comparison to when ATCC 202177 was present (FIG. 4B). Thus, the data presented in FIGS. 4A and 4B clearly indicate that ATCC 202177 reduces the hydrogen sulfide concentration in a given stream to an undetectable range, while not affecting the useful components of the gas stream.

Example 6

Removal of Hydrogen Sulfide by ATCC 202177 in the Presence of Ammonia

Figure 6A:
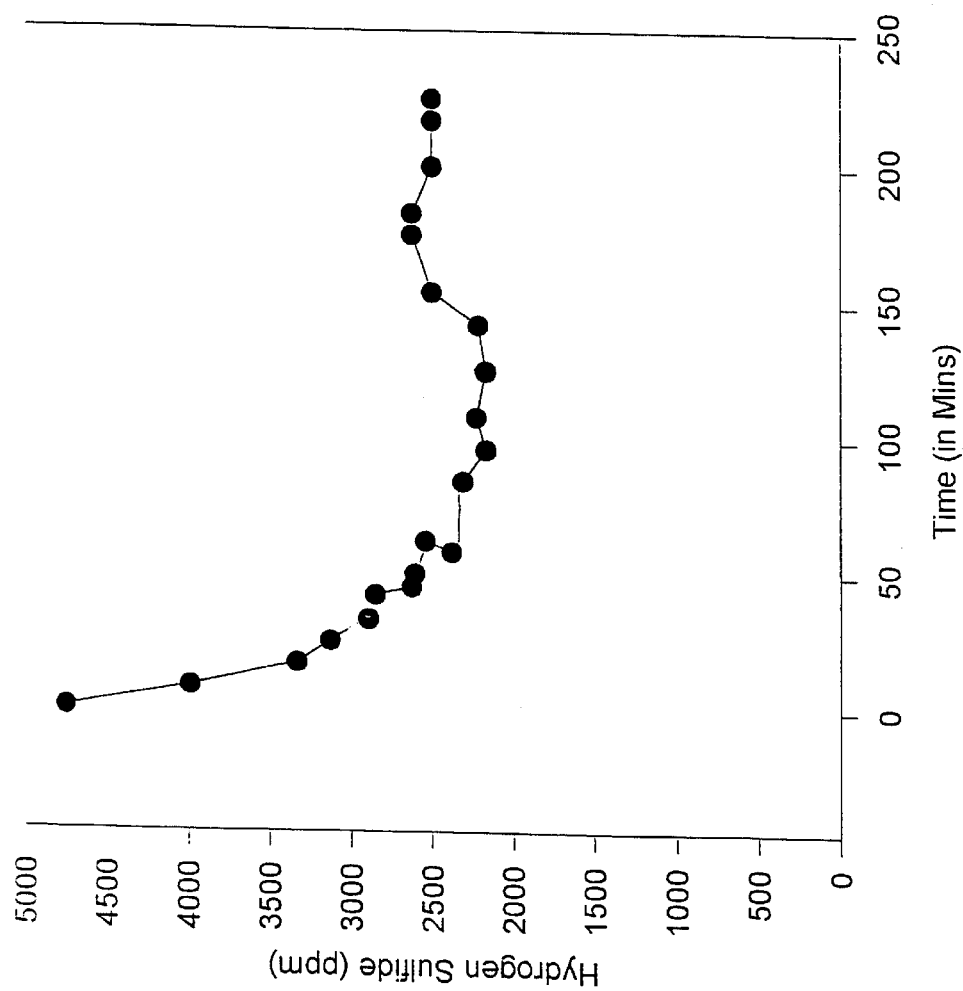
FIG. 6A illustrates hydrogen sulfide removal by ATCC 202177 in the presence of a fuel or other gas containing ammonia (200 ppm), carbon dioxide, carbon monoxide, hydrogen, methane, and nitrogen.
Figure 6B:
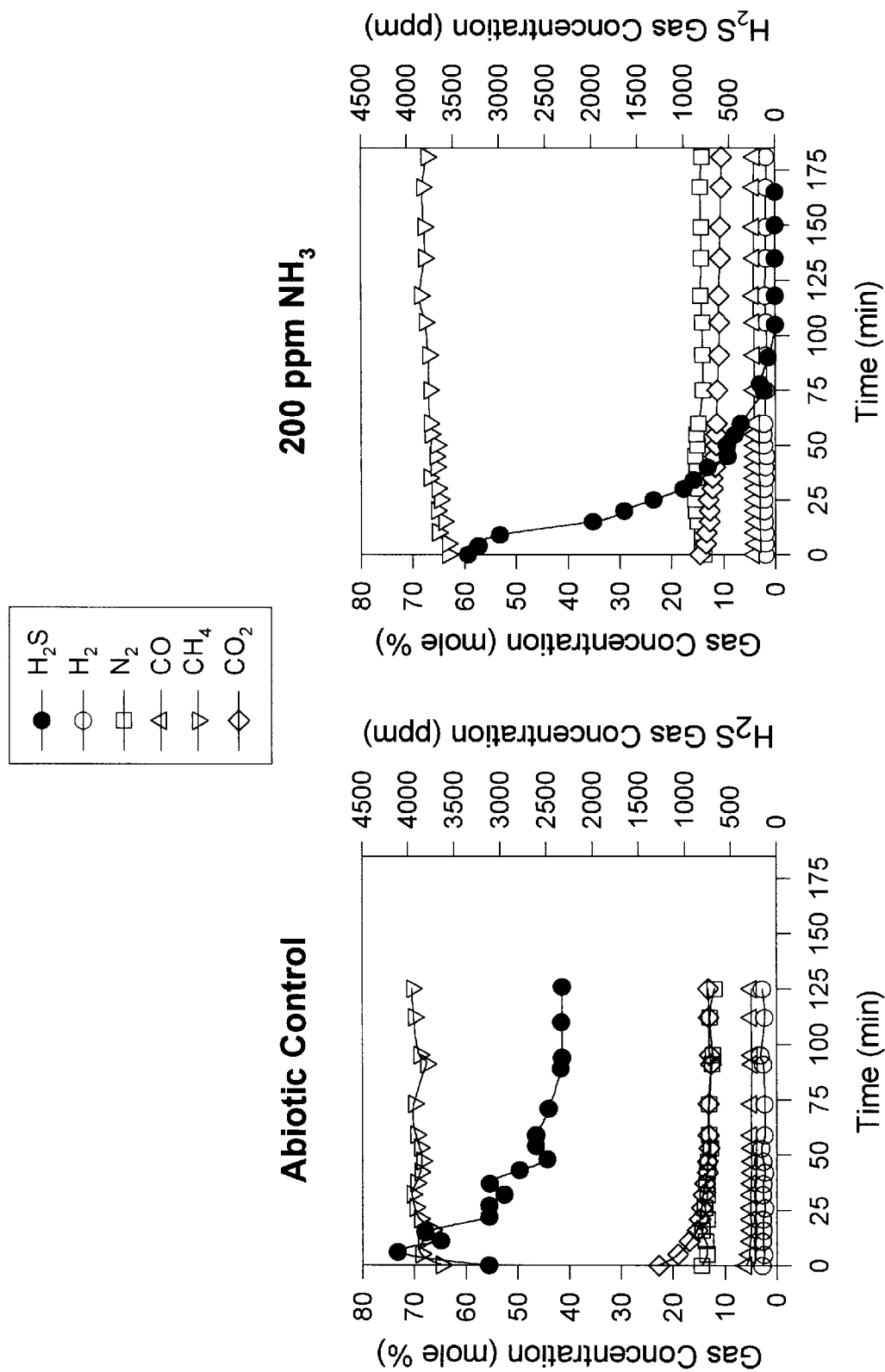
FIG. 6B illustrates comparative hydrogen sulfide removal in the presence of ammonia by enriched ATCC 202177 and without ATCC 202177.

The effect of ammonia on the growth of ATCC 202177 and removal of hydrogen sulfide by ATCC 202177 was evaluated by first growing the consortium at 100–200 ppm liquid ammonia added to TSN medium. The growth was evaluated as OD460 measurement. The data shown in FIG. 5 show that ATCC 202177 enriched in the presence of ammonia was not inhibited by up to 200 ppm ammonia. The effect on the removal of hydrogen sulfide at 68.03 atm was tested according to the method presented in Example 4, except that liquid ammonia at 200 ppm concentration was mixed in the TSN containing 60 g of enriched ATCC 202177 when the Parr reactor was charged. The data shown in FIG. 6B show that ATCC 202177 removes the hydrogen sulfide to zero ppm in about 70 minutes, in contrast to un-enriched ATCC 202177, as shown in FIG. 6A.

Example 7

Removal of Hydrogen Sulfide in the Presence of Cyanide

Figure 7:
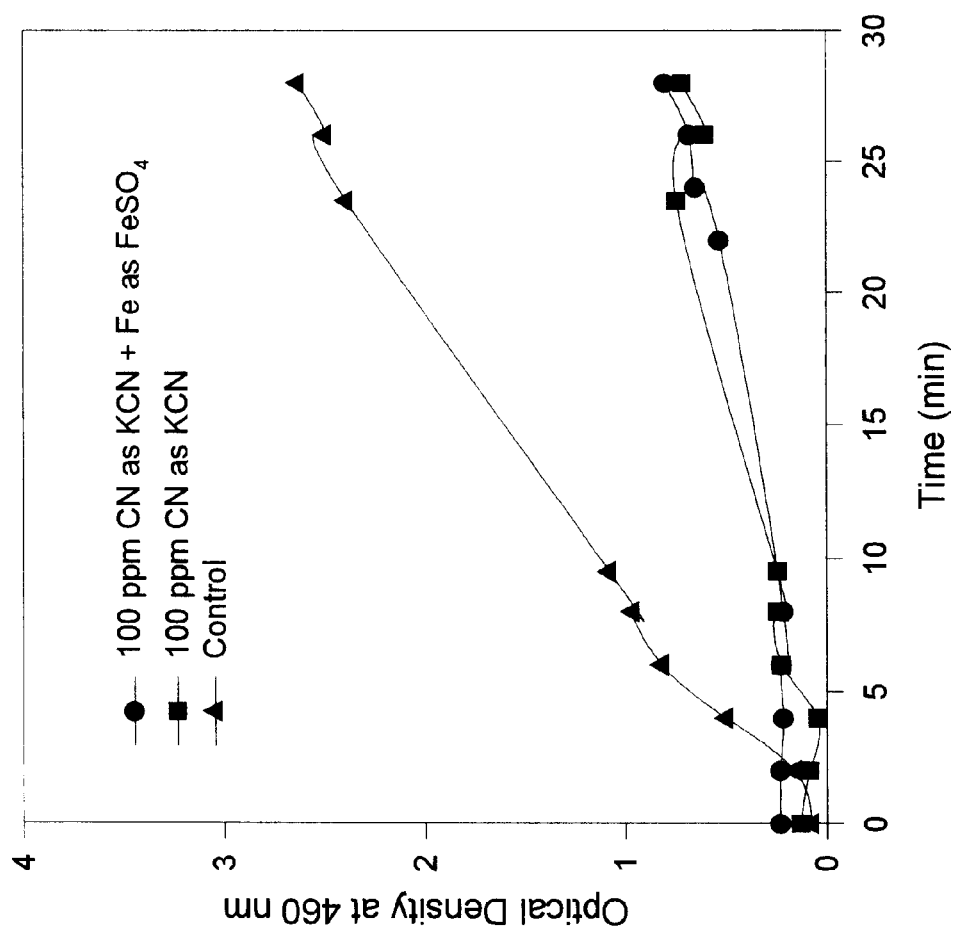
FIG. 7 shows that growth of un-enriched ATCC 202177 is inhibited by even 50 ppm of cyanide as potassium cyanide.
Figure 8:
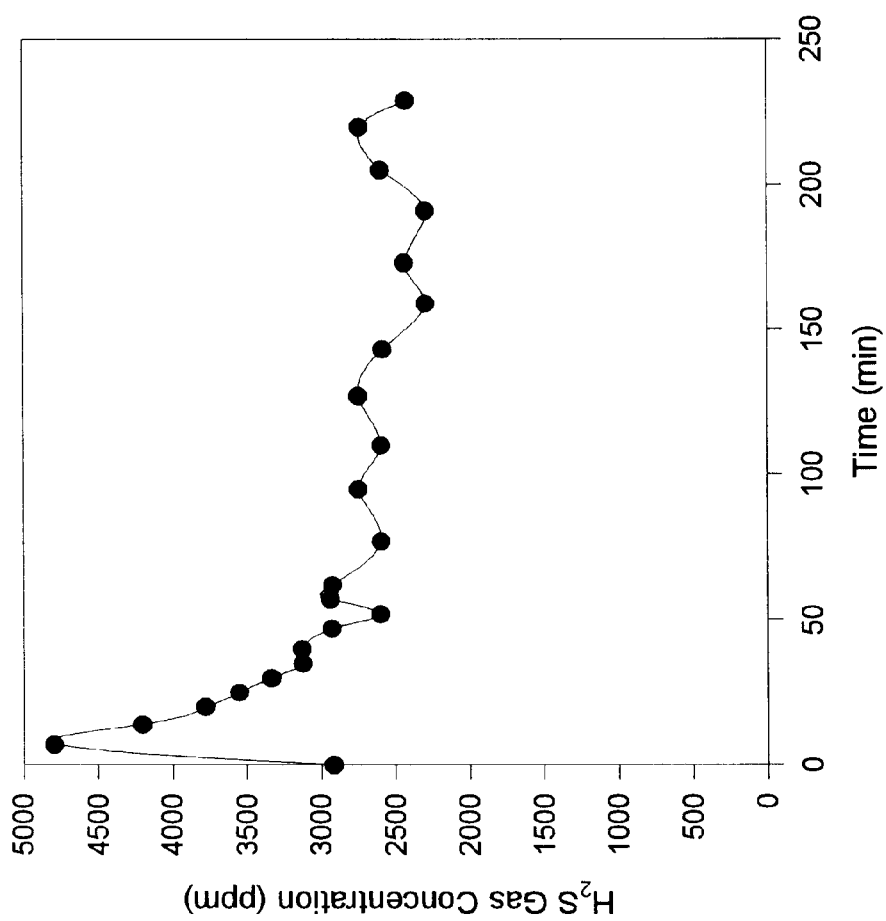
FIG. 8 shows that cyanide as potassium cyanide inhibits removal of hydrogen sulfide by un-enriched ATCC 202177.
Figure 9:
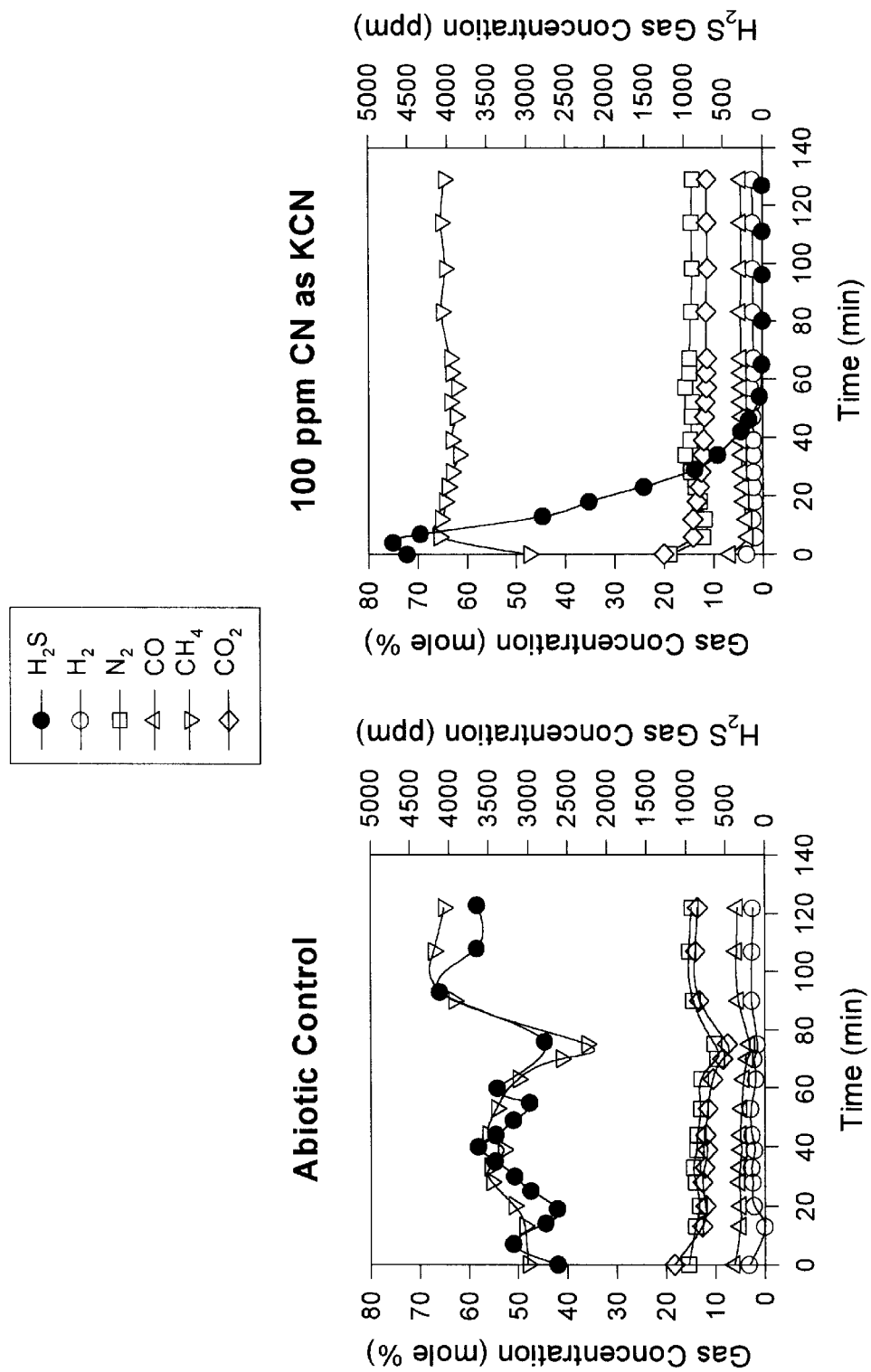
FIG. 9 shows that enriched ATCC 202177 removes hydrogen sulfide from a gaseous mixture containing carbon dioxide, carbon monoxide, cyanide (up to 100 ppm as potassium cyanide), hydrogen, methane, and nitrogen.
Figure 10:
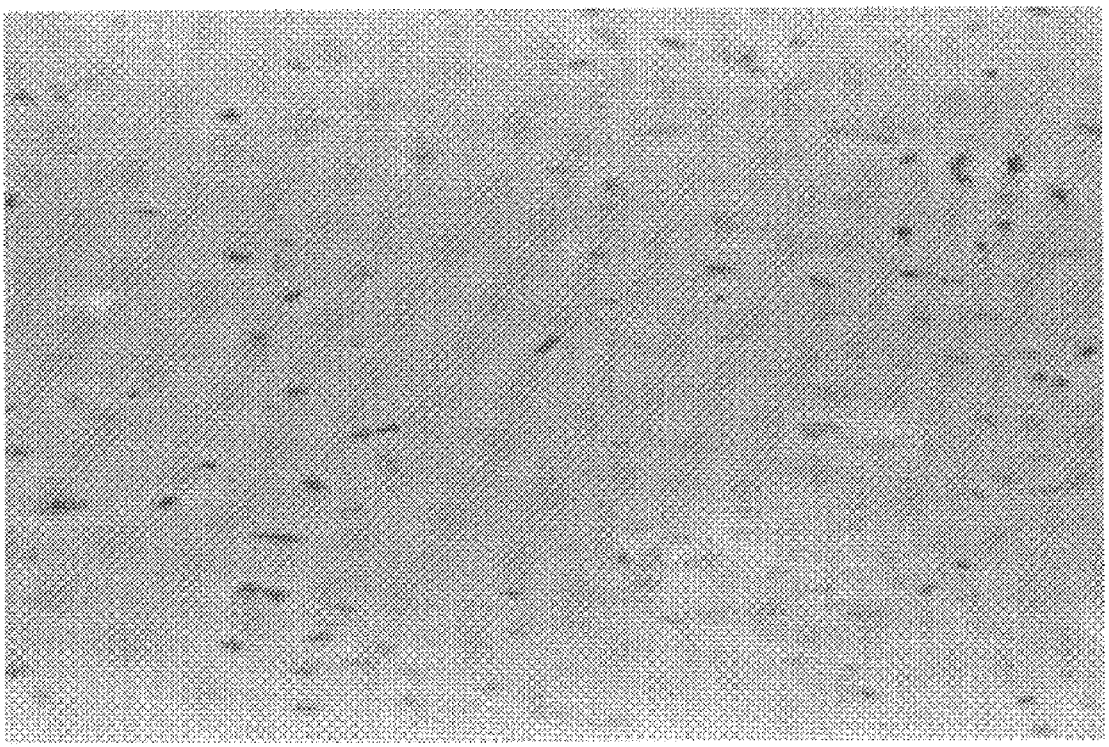
FIG. 10 is a photomicrograph of the consortium ATCC 202177.

This experiment was conducted in the same manner as Example 5. Initial data show that even at 50 ppm loading, cyanide inhibited the growth of ATCC 202177 (FIG. 7), and ATCC 202177 not enriched by cyanide was not capable of removing hydrogen sulfide (FIG. 7). The tolerance of ATCC 202177 to 100 ppm cyanide as potassium cyanide was modified according to the method of Example 5 by enriching ATCC 202177 in TSN medium supplemented with potassium cyanide. The data shown in FIG. 8 show that hydrogen sulfide removal by this enriched ATCC 202177 in the presence of potassium cyanide is not inhibited.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Cadenhead et al, "Oxidation of Hydrogen Sulfide by Thiobacilli", *Biotech. Bioeng.* 35:1150–1154 (1990)

Cork et al, "Acid-Gas Bioconversion Favors Sulfur Production", *Biotech. and Bioeng. Symp.* 12:285–290 (1982)

Dalrymple et al, "An Overview of Liquid Redox Recovery", *Chemical Engineering Progress,* pp. 43–49 (May 1989)

Dalrymple et al, "Research Summary", Proc. 1995 GRI Liquid Redox Sulfur Recovery Conference, Austin, Tex., pp. v–x (1996)

Gadre, "Removal of Hydrogen Sulfide from Biogas by Chemoautotrophic Fixed-Film Bioreactor" *Biotechnol. Bioeng.* 34:410–414 (1989)

Leppin et al, "Gas Research Institute Program in Sulfur Recovery Research", Proc. GRI Liquid Redox Sulfur Recovery Conference, Austin, Tex., pp. 387–411 (1991)

Leppin, "Overview of Liquid Redox Sulfur Recovery and $H_2S$ Scavenging Processes", Proc. 1995 GRI Liquid Redox Sulfur Recovery Conference, Austin, Tex., pp. 3–10 (1996)

Leppin, "Overview of GRI's Sulfur Recovery Research Program", Proc. 1995 GRI Liquid Redox Sulfur Recovery Conference, Austin, Tex., pp. 11–16 (1996)

McCarthy, "Lignocellulose-degrading Actinomycetes", *FEMS Microbiol. Rev.* 46:145 (1987)

McManus, "The Development, Chemistry and Applications of Chelated Iron Sulfur Recovery Processes", 3rd Int'l Petroleum Environmental Conference, Albuquerque, N. Mex., Sep. 24–27, 1996

Plas, et al, "Ratio of Biological and Chemical Oxidation During the Aerobic Elimination of Sulfide by Colorless Sulfur Bacteria", *All Microbiol. Biotechnol.* 36:817–822 (1992)

Quinlan et al, "Technical and Economic Comparison of I.O-CAT II° with other iron-based Liquid Redox Processes", Proc. 1992 GRI Liquid Redox and Sulfur Recovery Conference, Austin, Tex., pp. 179–220 (1993)

Quinlan et al, "Evaluation of ARCTECH's Biological Process for $H_2S$ Removal", Gas Research Institute Report for the Contract #5088-221-753, 18 pages Rehmat et al, BIO-SR Technology Update", Proc. 1995 GRI Liquid Redox Sulfur Recovery Conference, Austin, Tex., pp. 41–55 (1995)

Srivastava, "Biological Removal of $H_2S$ from Sour Natural Gas", Proc. 1992 GRI Liquid Redox Sulfur Recovery Conference, Austin, Tex., pp. 131–146 (1993)

Srivastava, "Saccharification of Lignocellulosic biomass by Actinomycetes: A Comparative Study with Meso- and Thermophiles", TAPPI Proc. Int'l Symp. Wood Pulping Chem., 2:227–232 (1989)

Srivastava et al, Proceedings of the 3rd Int'l Petroleum Environmental Conference, pp 705–729 (1996)

Sublette et al, "Microbial Desulfurization of Gases", *Biotechnol. Bioeng. Symp.* 17:543–564 (1986)

Suzuki et al, *Proc. Natl. Acad. Sci.* 45:239 (1959)

What is claimed is:

1. A method for preparing an enriched culture of microbial consortium ATCC 202177 by:
   a) contacting said consortium ATCC 202177 with an organic nitrogen source; one or more gaseous sulfur compounds; at least one compound selected from the group consisting of ammonia, carbon dioxide, carbon monoxide, hydrogen cyanide, methane, higher gaseous hydrocarbons, and mixtures thereof; and a mineral salt solution as a nutrient medium for the microorganisms;
   b) maintaining the microbial consortium of step a) in the nutrient medium for a time sufficient to obtain an enriched consortium ATCC 202177 which reproducibly metabolizes sulfur compounds in a gas stream containing at least one of ammonia, carbon dioxide, carbon monoxide, hydrogen cyanide, methane, higher gaseous hydrocarbons, nitrogen and mixtures thereof;
   c) recovering said enriched consortium ATCC 202177 consortium of step b).

2. The method according to claim 1, wherein said one or more gaseous sulfur compounds is selected from the group consisting of sulfur compounds which are sulfides, thiosulfates, thionates, thionites, and mixtures thereof.

3. The method according to claim 1 wherein the pH of the nutrient medium during the growth of the microorganisms in said nutrient medium is maintained in the range of pH 6.8–8.0 for a time sufficient to obtain the enriched consortium ATCC 202177 which reproducibly metabolizes sulfur compounds.

4. A method for desulfurizing a gas stream containing one or more gaseous sulfur compounds and at least one compound selected from the group consisting of ammonia, carbon dioxide, carbon monoxide, hydrogen cyanide, methane, higher gaseous hydrocarbons, nitrogen, and mixtures thereof; the method for desulfurizing comprising:
   (a) contacting said gas stream with an aqueous nutrient medium loaded with an enriched culture of microbial consortium ATCC 202177, said enriched consortium ATCC 202177 consortium prepared by a method comprising:
      (i) contacting a consortium of ATCC 202177 with an organic nitrogen source; one or more gaseous sulfur compounds; at least one compound selected from the group consisting of ammonia, carbon dioxide, carbon monoxide, hydrogen cyanide, methane, higher gaseous hydrocarbons, nitrogen, and mixtures thereof, and a mineral salt solution as a nutrient medium for the microorganisms;

(ii) maintaining the microbial consortium of step (i) in the nutrient medium for a time sufficient to obtain an enriched consortium ATCC 202177 which reproducibly metabolizes sulfur compounds in a gas stream in the presence of at least one of the compounds selected from ammonia, carbon dioxide, carbon monoxide, hydrogen cyanide, methane, higher gaseous hydrocarbons, nitrogen and mixtures thereof;

(iii) recovering said enriched consortium ATCC 202177 of step (ii); and (b) keeping the gas stream to be desulfurized in contact with said enriched consortium ATCC 202177 consortium until the gaseous sulfur compounds in the gas stream are oxidized to elemental sulfur by the enriched consortium ATCC 202177.

5. The method according to claim 4 wherein the pH of the nutrient medium during the growth of the microorganisms in said nutrient medium is maintained in the range of pH 6.8–8.0 for a time sufficient to obtain the enriched consortium ATCC 202177 which reproducibly metabolizes sulfur compound and the pH of the mixture during desulfurization is maintained between 6.8 and 8.0.

6. The method according to claim 4, wherein the nutrient medium comprises a) at least one organic nitrogen source selected from the group consisting of yeast extract, soy flour, cottonseed flour, and animal proteins; and b) a solution of at least one mineral salt selected from the group consisting of ammonium sulfate, boric acid, calcium chloride, cobalt chloride, copper (II) sulfate, ferric chloride, magnesium sulfate, manganese sulfate, potassium nitrate, potassium nitrite, dihydrogen potassium phosphate, sodium bicarbonate, sodium disulfite, sodium molybdate, sodium tungstate, zinc sulfate, and mixtures thereof.

7. The method according to claim 4 wherein the enrichment process is conducted at a temperature between about 10 C. and 60 C.

8. The method according to claim 4 wherein the microbial consortium of step b) is maintained at a pressure between 1 and 80 atmospheres.

9. The method according to claim 4, wherein the mass to volume ratio of the enriched ATCC 202177 consortium to the nutrient medium is between about 3.5 g/L and 200 g/L.

10. The method according to claim 4, wherein the gas contains ammonia.

11. The method according to claim 4, wherein the gas contains cyanides.

12. The method according to claim 4, wherein the gas contains fuel gases.

13. The method according to claim 4, wherein the gas is selected from the group consisting of natural gas, syngas, landfill gas, biogas, geothermal gas, industrial gas, and tail gas.

14. The method according to claim 4 wherein the desulfurization is effected at pressures ranging from about 75 to about 1000 psi.

* * * * *